(12) United States Patent
Brown

(10) Patent No.: US 6,769,631 B2
(45) Date of Patent: Aug. 3, 2004

(54) COMBINATION AIR FRESHENER AND HAND LOTION DISPENSER

(75) Inventor: Douglas S. Brown, Toledo, OH (US)

(73) Assignee: Fresh Products, Inc., Toledo, OH (US)

( * ) Notice: Subject to any disclaimer, the term of this patent is extended or adjusted under 35 U.S.C. 154(b) by 301 days.

(21) Appl. No.: 09/951,112

(22) Filed: Sep. 10, 2001

(65) Prior Publication Data

US 2002/0030116 A1 Mar. 14, 2002

Related U.S. Application Data

(60) Provisional application No. 60/231,256, filed on Sep. 8, 2000.

(51) Int. Cl.$^7$ ................................................ B05B 15/00
(52) U.S. Cl. ........................... 239/289; 239/34; 239/57; 239/333; 222/192
(58) Field of Search ............................... 239/53, 55, 56, 239/57, 58, 59, 333, 337, 289; 222/192, 321.7

(56) References Cited

U.S. PATENT DOCUMENTS

| | | |
|---|---|---|
| 3,269,605 A | 8/1966 | Silver |
| 3,375,538 A | 4/1968 | Mains et al. |
| 3,833,149 A | 9/1974 | Iozzio |
| 3,902,637 A | 9/1975 | Scheeler |
| 4,039,104 A | 8/1977 | Mijares, Jr. et al. |
| 4,636,328 A | 1/1987 | Flynn et al. |
| 4,709,425 A | 12/1987 | Bavaveas |
| 4,743,406 A | 5/1988 | Steiner et al. |
| 4,808,347 A | 2/1989 | Dawn |
| 4,821,923 A | 4/1989 | Skorka |
| 4,905,112 A | 2/1990 | Rhodes |
| 5,115,945 A | 5/1992 | Ruck |
| 5,165,603 A | 11/1992 | Hahn |
| 5,186,360 A | 2/1993 | Mease et al. |
| 5,223,182 A | 6/1993 | Steiner et al. |
| 5,284,272 A * | 2/1994 | Wei ............................ 222/192 |
| 5,367,716 A | 11/1994 | Huang |
| 5,379,917 A | 1/1995 | Brown et al. |
| 5,487,877 A | 1/1996 | Choi |
| 5,595,324 A | 1/1997 | Brown et al. |
| 5,690,255 A | 11/1997 | White |
| 5,791,525 A | 8/1998 | Fan |
| 5,799,826 A | 9/1998 | Brown et al. |
| 6,062,425 A | 5/2000 | Brown et al. |
| 6,569,387 B1 * | 5/2003 | Furner et al. ................. 239/57 |

OTHER PUBLICATIONS

Advertisements dated Sep. 20, 1989 and Jan. 20, 1998 and undated advertising materials showing a combination soap and air freshener dispenser.

* cited by examiner

Primary Examiner—Steven J. Ganey
(74) Attorney, Agent, or Firm—Knobbe, Martens, Olson & Bear, LLP

(57) ABSTRACT

A method and apparatus for dispensing of hand lotion and air freshener in a combined unit for home and office. Air freshener may be passively dispersed at a controlled rate from the apparatus, or may be actively dispersed when a user pumps the apparatus to receive a measured quantity of hand lotion. Dispersion may be implemented using a mechanical fan or compression of a sponge, for example.

3 Claims, 13 Drawing Sheets

COMBINATION AIR FRESHENER AND HAND LOTION DISPENSER

PRIORITY INFORMATION

This application is related to, and claims priority from, U.S. Provisional Patent Application No. 60/231,256 filed Sep. 8, 2000, the entire contents of which are incorporated by reference herein.

BACKGROUND OF THE INVENTION

1. Field of the Invention

The present invention relates to air fresheners and supply units therefore.

2. Description of the Related Art and Summary of Invention

Air fresheners are frequently used in home and business to control odors in bathrooms, kitchens, and other enclosed spaces. Generally, commercial dispensers for air fresheners can operate passively through ventilation and diffusion, or actively through electrical heating elements or mechanical fan assemblies. Because air freshener dispensers function by releasing a scent through evaporation or atomization, such dispensers work most effectively when placed in the open on a counter, table, or wall. They are nevertheless often hidden from view due to their odor eliminating purpose, where they are both less effective and more difficult to replace.

Numerous methods have been developed to improve air freshener dispensers for the home and business. Electrically powered and wall mounted dispensers are common. U.S. Pat. No. 4,808,347 to Dawn discloses an air freshener with a battery powered fan for deodorization of automobiles. Similarly, U.S. Pat. No. 4,743,406 to Steiner et al. describes a self-contained dispenser which uses replaceable cartridges of air freshener, and applies a battery powered fan to actively vent air past the cartridge. Air freshener dispensers have even been applied to common cassette tapes, as disclosed in U.S. Pat. No. 4,905,112 to Rhodes, in part to deodorize automobiles in a discrete and clever fashion. Unfortunately, none of these solutions provide an ideal solution for the home, office or storefront, as many require electric power, often necessarily with replacement of batteries as well as air freshener. These solutions usually do not suit themselves to placement in visible areas where such air freshener dispensers would be most effective.

Hand lotion, on the other hand, is commonly provided in home and business environments to moisturize, smooth, and improve the condition of skin. It is often available in disposable consumer pour or pump dispensers, or sometimes in wall units for commercial application. Consumer dispensers are commonly placed on tables, in kitchens, and in bathrooms, and do not have the less desirable appearance and connotation of an air freshener dispenser.

Applicant is one of the named inventors for U.S. Pat. No. 5,799,826, in which a dual dispenser was disclosed. That dual dispenser was disclosed as being used with soap and air freshener. This combination of soap and air freshener in a single dispenser was highly innovative for soap. When used with standard soap (which is rinsed off), rather than a sanitizer soap (which is not rinsed off), the dispenser is desirably placed reasonably near a source of water to allow washing off the soap after use. As standard soaps are by far the most popular, the placement of standard soap dispenser is limited, as it is impractical in non-washroom settings such as the coffee table, office desk, or the automobile.

Accordingly, a preferred embodiment is a dispenser that can be placed virtually anywhere in the home or office. Another aspect of a preferred embodiment is a dispenser for both air freshener and a liquid, such as hand lotion or soap, that avoids the difficulties of prior individual and combined dispensers while providing advantageous improvements in both structure and function.

Most retail, or consumer-oriented, air fresheners operate on an "always on" basis. That is, once the air freshener is initially activated, it dispenses fragrance until its supply is exhausted. Because air freshening is typically only necessary when a person is in the same general area as the air freshener dispenser, the "always on" dispensers may result in a majority of the fragrance being dispensed when it is not necessary or desired.

Further, the dispensed fragrance, along with most other odors, are only noticeable to a person for a short time after the smell is encountered. After this initial period, the person becomes accustomed to the fragrance and it no longer produces the desired sensory response. More user oriented consumer air fresheners are available, such as spray-type products, for example. However, the necessary mechanisms to propel the air freshener often make spray-type dispensers relatively expensive and difficult to recycle.

Accordingly, a preferred dispenser dispenses only a small amount of fragrance, if any, until the dispenser is user-actuated. Advantageously, such an arrangement avoids desensitization, thus increasing the perceived effectiveness of the air freshener. In addition, such a dispenser avoids unnecessary dispensing of fragrance, thereby increasing the useful life of the fragrance. Moreover, such a dispenser provides both a pourable compound, such as hand lotion, and air freshener in a single product, which is less costly than purchasing hand lotion and air freshener separately. In addition, less packaging materials are utilized in comparison to separate products, thereby reducing the amount of material disposed of or needing to be recycled at the end of the product life.

A preferred embodiment is an assembly including a dispenser. The dispenser includes a container and an actuator, which defines an actuation surface. A pourable compound is held within the container and is dispensible from the container upon manual manipulation of the actuation surface. A base defines a substantially flat mounting surface and an interior surface sized and shaped to receive and retain the dispenser. The base also includes a location sized and shaped to receive a supply of air freshener wherein the supply of air freshener is received by the location.

A preferred embodiment is an air freshener delivery assembly. The assembly includes a bottle, a hood and a supply of air freshener. The hood includes a wall cooperating with at least a portion of the bottle to form a cavity. The supply of air freshener is positioned within the hood. In addition the hood is movable with respect to the bottle from a first position, wherein the hood and the bottle cooperate to define a first generally enclosed volume, to a second position wherein the hood defines a second enclosed volume smaller than the first enclosed volume, thereby dispensing air freshener from the supply of air freshener.

A preferred embodiment is an assembly including a first engagement portion defining a cavity and an actuator defining an actuation surface. A pourable compound is positioned within the first engagement portion, wherein the compound is dispensible from the first engagement portion upon manual manipulation of the actuation surface. The assembly also includes a second engagement portion, which defines an interior surface sized and shaped to receive and retain the first engagement portion. The second engagement portion also defines a location sized and shaped to receive a supply of air freshener, which is positioned at the location.

A preferred embodiment is an assembly including a first engagement portion defining a cavity and an actuator defining an actuation surface. A supply of hand lotion is placed within the first engagement portion, wherein the supply of hand lotion is dispensible from the first engagement portion upon manual manipulation of the actuation surface. A second engagement portion defines a location sized and shaped to receive a supply of air freshener and a supply of air freshener is positioned at the location.

A preferred embodiment is a dispenser assembly including a first portion at least partially defining a first enclosure for receiving a supply of hand lotion. A second portion at least partially defines a second enclosure for receiving a supply of air freshener. The second portion has at least one opening and is movable relative to the first portion to a dispensing position for urging the air freshener in a direction from within the second enclosure toward the opening. A pump assembly communicates with the supply of hand lotion and defines an outlet positioned outside of both the first and second enclosures. The hand lotion is urged in a direction from within the first enclosure toward the outlet when the pump assembly is actuated. The second portion is movable to the dispensing position independent of the actuation of the pump assembly.

A preferred embodiment is a dispenser assembly including a first portion at least partially defining a first enclosure for receiving a supply of hand lotion. A second portion at least partially defines a second enclosure for receiving a supply of air freshener. The second portion has at least one opening. A pump assembly communicates with the supply of hand lotion and defines an outlet positioned outside of both the first and second enclosures. The hand lotion is urged in a direction from within the first enclosure toward the outlet when the pump assembly is actuated. A means is provided for dispensing the air freshener from within the second enclosure through the opening without an external supply of power.

A preferred embodiment is a dispensing base for use with a liquid dispenser and an air freshener enclosure. The base includes a substantially flat mounting surface and an interior surface sized and shaped to receive the liquid dispenser. The base also includes a location sized and shaped to receive the air freshener enclosure. The base defines at least one hole through which air freshener from the air freshener enclosure can be dispersed.

Another aspect of a preferred embodiment is a combination air freshener and hand lotion dispenser that permits direct user control of the strength and quantity of scent released in relation to dispensing of hand lotion.

Yet another aspect of a preferred embodiment is a combination air freshener and hand lotion dispenser in which the supplies of hand lotion and/or air freshener are refillable or replaceable independently or as a unit.

Still another aspect of a preferred embodiment is a combination air freshener and hand lotion dispenser where the dispensing of hand lotion, for example through a pump, is used to indirectly power the release of air freshener through a mechanically powered or passive ventilation system.

Finally, yet still another aspect of a preferred embodiment is a combination air freshener and hand lotion dispenser where the release of air freshener and dispensing of hand lotion are independently controllable.

Hand lotion is often dispensed in pour, squeeze, or pump bottles for home and business environments, where those bottles are usually disposable. As is known by those of skill in the art, hand lotion may include various combinations of moisturizers, oils and emollients, and may include nutritive elements such as Vitamin A, Vitamin E or Aloe Vera. While hand lotion may be scented, its primary function is placement directly on the hands to improve the skin's condition. Hand lotion generally does not have to be washed off the hands after use, as with standard soap. It does not function efficiently as an air freshener, and would be ineffective and messy if used as such. Hand lotion is an emulsion of primarily water and various oils, with lecithin typically being at least one of the emulsifying agents. If skin renewal properties are desired, the lotion may contain 2–8% of an alpha or beta hydroxy ingredient, to promote exfoliation.

Air freshener means any entity designed for the purpose of masking odors, or freshening, cleaning or deodorizing the air. The main ingredient of most air fresheners is a fragrance. Air fresheners previously had a chemical composition consisting of 10–25% fragrance, although substantially more or less fragrance, between 1–99% would be present depending on the strength of the resulting scent, the placement and purpose of the air freshener and the type of carrier the fragrance is placed within. Carriers for fragrance may include, for example, an odorless mineral spirit to dilute and aid in evaporating the fragrance, polymer gel, or a semisolid wax, which evaporates the fragrance at ambient temperature or upon heating. A porous surface frequently is used to prevent leakage but allow diffusion of fragrance into the surrounding environment, including, for example a polyester matrix in which the fragrance and carrier can be suspended. In 1997, the EPA established Volatile Organic Compound (VOC) content limits for air fresheners. Since fragrances very often contain VOC, these limits must be considered in the process of air freshener design. However, VOC content limits do not apply to air fresheners whose VOC constituents consist of 100% fragrance. This latter kind of air freshener can contain any desired amount of fragrance (0–100%).

Preferred embodiments realize an advantageous combination air freshener dispenser and hand lotion dispenser. A preferred embodiment includes a method for combining a hand lotion dispenser and air freshener dispenser to allow control of air freshener diffusion based on dispensing of hand lotion, or, alternatively, passively diffusing air freshener through controlled continuous ventilation. Both methods may be combined in the same apparatus. This can be accomplished through a number of physical embodiments, the preferred of which are described below.

A preferred embodiment includes an apparatus for combining a hand lotion dispenser and air freshener dispenser to allow subtle continuous dispensing of air freshener passively through the use of one or more adjustable vents. Thus, within one embodiment of a dispenser, at least two vent units are included where one of the vents is moveable with respect to the other. The vent units may have one or more openings in each which allow communication of fragrance from the air freshener enclosure to the outside environment. For example, the vent units may include surfaces which can be separated on user operation creating an opening for communication of fragrance to the outside environment. By manually adjusting the moveable vent unit, a user can regulate the rate of diffusion of fragrance into the surrounding environment and hence control the strength of scent from the air freshener dispenser.

Alternatively, at least one vent unit is included in the unit, where at least one vent unit is moveable to create an opening between the surface of the vent unit and the base of the dispenser for ventilation of air freshener. For example, the moveable vent may be automatically adjusted on user pumping of the hand lotion dispenser to dispense hand lotion in additional embodiments of the present invention. A preferred dispenser is particularly convenient for private use, as it can be placed anywhere in the home or office and is fully adjustable with respect to dispensing of hand lotion and release of air freshener.

A preferred embodiment also includes an apparatus for combining a hand lotion dispenser and air freshener dispenser in such a manner as to allow dispensing of air freshener actively through a number of optionally non-electrified mechanisms initiated by a user's pump action when dispensing hand lotion. Such an apparatus allows for but removes the need for batteries or electrification of the unit, while providing a controlled, active ability to diffuse fragrance. In one preferred embodiment, depression of the hand lotion pump handle provides a measured quantity of hand lotion as would a standard pump mechanism, but also affects a release of air freshener through compression of a mechanical energy transferring device.

Preferably, within the vent unit, or alternatively in the vent units or base unit, a resilient sponge and, optionally, a flat plate can be placed beneath the air freshener enclosure, where the plate can be attached to the pump tube such that depression of the pump handle depresses both the pump tube and the flat plate. Depression of the flat plate compresses the resilient sponge, allowing the release of fragrance currently held within the sponge to the outside environment through the opening or openings in or between the vent units. When the pump handle is released, the flat plate releases the sponge, and the sponge expands and draws in more fragrance from the air freshener enclosure. A spring may optionally be used to complement the resilient sponge, such that the spring is placed around the pump tube in a manner that the spring is compressed when the pump handle is depressed, and releases its stored energy when the pump handle is released, thus providing greater expansion and fragrance input into the uncompressed sponge. Alternatively, the flat plate may be omitted by the use of an air freshener enclosure having a surface suitable to adequately compress the sponge.

A similar result can be achieved by use of a mechanical fan assembly placed above or below the air freshener enclosure within the vent unit or units. When the pump handle is depressed, the downward force is transferred to the pump tube and the mechanical fan assembly, which translates the downward force into a rotational force acting on the fan. The fan then spins for a brief, adjustable time during which fragrance is drawn from the air freshener enclosure, and between or out of the vent unit or vent units, and or base unit, into the outside environment.

In addition, it is contemplated to substitute a manual pump arrangement for the above-described mechanical fan assembly. In such an arrangement, the vent unit surrounds the upper portion of the base unit and creates a cavity to house the air freshener enclosure. The vent unit is capable of sliding relative to the base unit, so that when the pump handle is depressed, the cavity volume is simultaneously reduced. This forces the air contained therein to be evacuated, and fragrance drawn from the air freshener enclosure to the outside environment, in a manner similar to the mechanical fan assembly. With this arrangement, the vent unit may be depressed individually, thereby releasing fragrance without dispensing hand lotion.

Alternatively, the vent unit may be placed below, and surround a lower portion of the base unit creating a cavity to house the air freshener enclosure below the base unit. In this arrangement, depression of the pump handle would dispense hand lotion, while depression of the base unit itself would force the evacuation of air from the cavity, and draw fragrance from the air freshener enclosure to the outside environment. Such an apparatus allows for active air freshening without the need for batteries, and at the same time allows for adjustment in the strength of fragrance released. As mentioned previously, the active and passive methods may be combined to allow a combination of continuous and user-initiated fragrance release at varying strengths depending on manual adjustment of the dispenser and environmental need.

DETAILED DESCRIPTION OF THE PREFERRED EMBODIMENT

Figure 1:
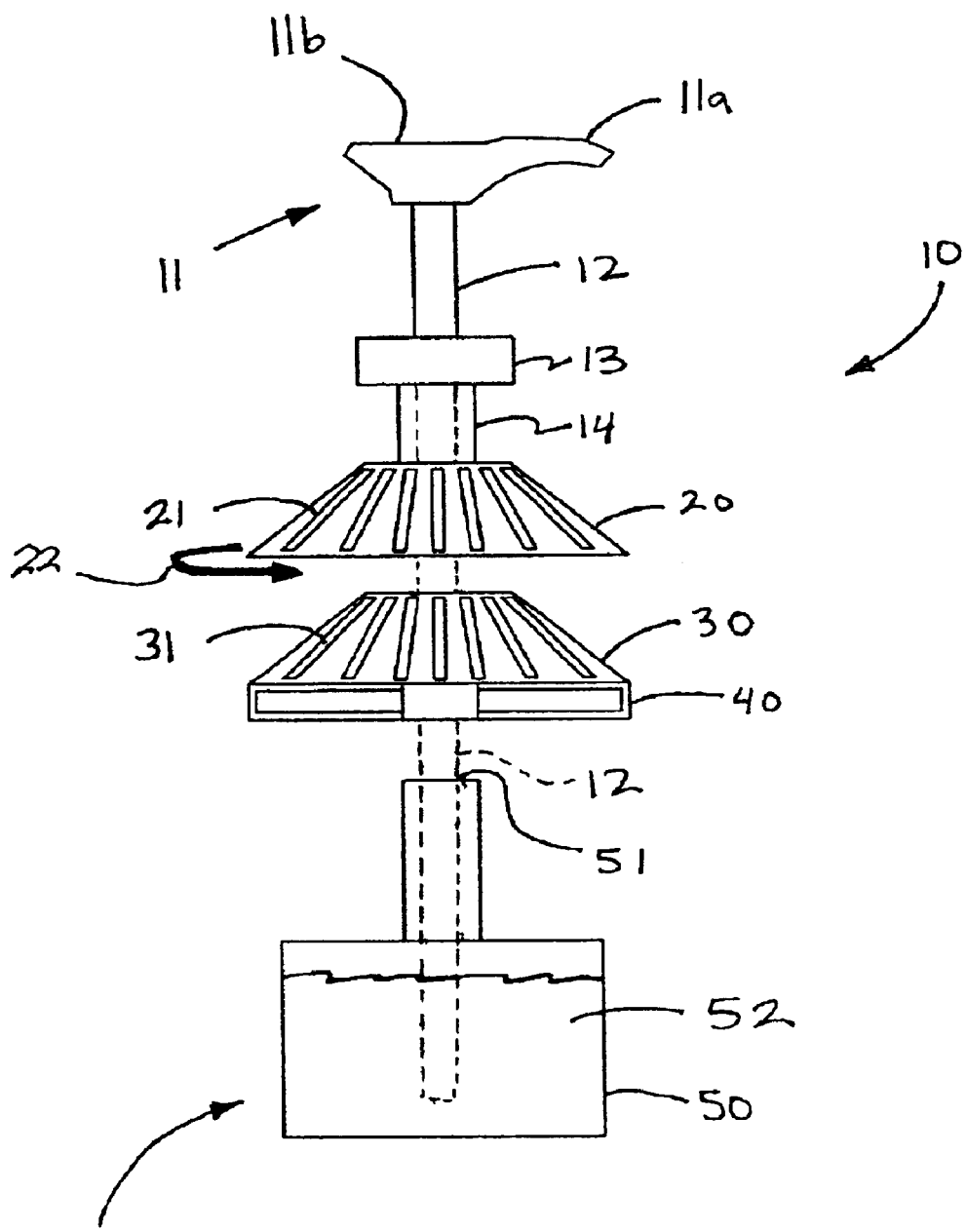
FIG. 1 is an exploded perspective view of one embodiment of a hand lotion and air freshener dispenser that utilizes a passive dispersion of air freshener.

With reference to FIG. 1, one embodiment of a combination hand lotion and air freshener dispenser 10 employing passive diffusion is detailed in an exploded view. The combination dispenser 10 comprises a base unit 53, with a pump handle 11 which defines a spout 11*a* for dispensing of hand lotion as well as a surface 11*b* for depression regulating pump action for dispensing of hand lotion. The pump handle 11 is connected to the inner spout tube 12, which extends from the pump handle 11 to the hand lotion enclosure 50. The inner spout tube reaches through the hand lotion enclosure opening 51 and then extends into the supply of hand lotion 52 inside the hand lotion enclosure 50.

The hand lotion enclosure 50 is defined by at least one distinct wall that creates a separate compartment in which hand lotion 52 may sit. Such a compartment may have any cup or bottle shape convenient to hold the hand lotion within the many possible shapes of the present invention. Such a compartment may be enclosed within or form the base unit 53 of the dispenser.

The inner spout tube 12, below the pump handle 11, may also be attached to an optional spout seal 13 and optional outer spout tube 14. When included, the spout seal at least partially surrounds the inner spout tube 12, and seals the top of the outer spout tube 14. The outer spout tube 14 surrounds the inner spout tube 12 from the spout seal 13 to some point before or at the end of the inner spout tube 12 in the hand lotion enclosure 50. As well known in the art, the pump mechanism of 11, 12, 13 and 14 creates a pressurized pump region on pressing of the pump handle 11b by depressing both the inner spout tube 12 which extends all the way to the pump handle 11 and the outer spout tube 14 which is sealed at the spout seal 13. In this manner hand lotion is dispensed at the pump handle spout 11a. More generally, any suitable pump mechanism for liquid may be provided.

Between the pump handle 11 and the hand lotion enclosure 50 and base 53 are an upper vent unit 20 and optional lower vent unit 30. Preferably, the upper vent unit consists of at least one surface at least partially surrounding the inner spout tube 12 and optional outer spout tube 14, where the optional spout seal 13 attaches to the upper vent unit 20 via a standard screw top, rubberized seal, or similar method known in the art. One or more ventilation holes 21 may be placed in the upper vent unit 20. Similarly, the lower vent unit 30 may contain one or a number of ventilation holes 31, where the optional lower vent unit 30 consists of at least one surface at least partially surrounding the inner and optional outer spout tubes 12 and 14.

The upper ventilation unit 20 is preferably capable of rotation with respect to the lower ventilation unit 30, as indicated by the arrow 22 in FIG. 1. The upper ventilation unit 22 is moveable between a fully closed position, where there is substantially no overlap between the vents 21 of the upper ventilation unit 20 and the vents 31 of the lower ventilation unit 30, and a fully open position, wherein there is substantially complete overlap of the vents 21 and 31. Additionally, the upper ventilation unit 20 may be positioned at substantially any desired position between the fully open and fully closed position. In this manner, the rate of passive evaporation of air freshener from the air freshener enclosure 40 may be adjusted. Alternatively, the upper vent unit 20 and lower vent unit 30 may be separable to create a ventilation opening between them.

The air freshener enclosure 40 at least partially surrounds the inner 12 and optional outer 14 spout tubes, and may lie between the optional lower vent unit 30 and hand lotion enclosure 50 or base 53 such that the upper 20 or optional lower vent unit 30 or base 53 may serve to completely enshroud the air freshener enclosure 40. The air freshener enclosure 40 may be removable 41, for example, by lifting the optional lower 30 and upper 20 vent units in order to expose the air freshener enclosure. In one of many variations of this embodiment, the air freshener enclosure 40 may lie between the upper vent unit 20 and optional lower vent unit 30, or between the upper vent unit 20 and hand lotion enclosure 50 or base 53.

The air freshener enclosure 40 may consist of fragrance suspended in a carrier, may expose a polyester matrix on one or more surfaces to allow evaporation of fragrance, and or may itself have one or a number of openings for release of fragrance. The air freshener enclosure 40 is preferably small enough to fit within the vent units 20 or 30, and base unit 53, and conform to one of the many shapes possible for the present invention.

Figure 2:
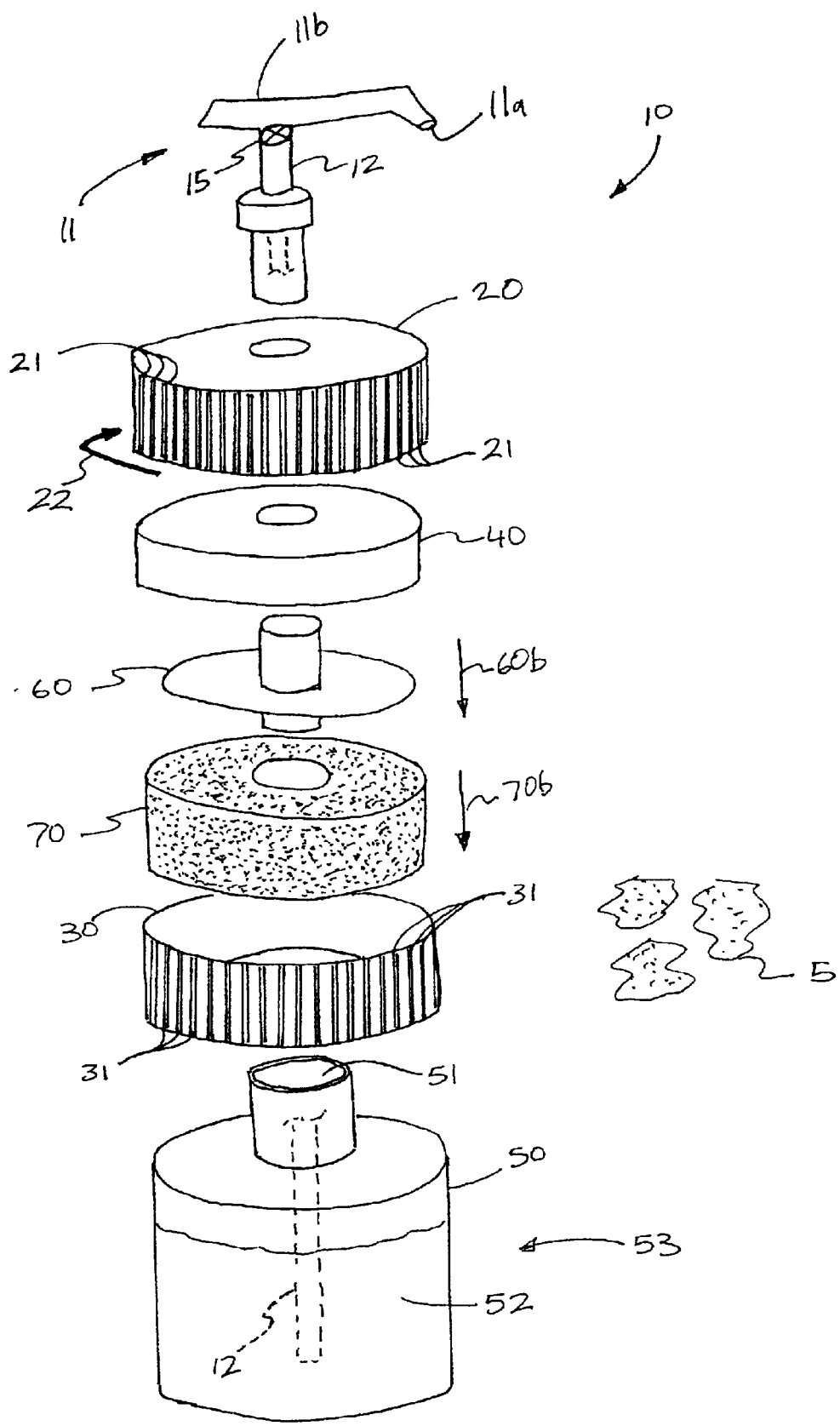
FIG. 2 is an exploded perspective view of a second embodiment of a hand lotion and air freshener dispenser that utilizes an active dispersion of air freshener using a sponge method.

A second embodiment of a dispenser 10 is illustrated in FIG. 2. A standard pump apparatus consisting of a pump handle 11 with pump spout 11a and a surface 11b for compression to initiate pump action is connected to an inner spout tube 12. The optional spout seal 13 similarly at least partially surrounds the inner spout tube 12 and seals the end of the optional outer spout tube 14.

The upper vent unit 20 and optional lower vent unit 30 may be similar to the first embodiment, except the vent unit or units 20 and 30 serve to enclose the air freshener enclosure 40, an optional circular plate defining a surface 60, and a resilient sponge 70. The three components 40, 60 and 70 may be placed in any order between the upper and lower vent units 20 and 30, but the placement of the air freshener enclosure 40 above the plate surface 60, with the plate surface 60 itself above the sponge 70, is preferred. Alternatively, the optional plate surface 60 may be omitted, and substituted with an air freshener enclosure 40 equipped with an appropriate surface to compress the resilient sponge 70. Thus, when such an arrangement is used, the air freshener enclosure 40 effectively functions as both an air freshening device and as the plate surface 60.

The air freshener enclosure 40 contains fragrance usually suspended in a carrier, and may be optionally removable. The air freshener enclosure 40 at least partially surrounds the inner 12 and optional outer 14 spout tubes and, in at least one preferred embodiment, does not move when the pump handle 11 is depressed 11b. It is small enough to fit within the vent unit or units 20 and or 30, and the base unit 53, and otherwise conforms to one of the many shapes possible for the current invention. The plate surface 60 is attached to the optional outer 14 and or inner 12 spout tubes such that when the pump handle 11 is depressed, the plate surface 60 is depressed 60b. The plate surface 60 at least partially surrounds the optional outer 14 and inner 12 spout tubes and when depressed 60b compresses the sponge 70b.

The resilient sponge 70 at least partially surrounds the optional outer 14 and inner 12 spout tube, and is sufficiently porous to allow air to leave the sponge when compressed and fill the sponge when decompressed. When the pump handle 11 is depressed 11b, the plate surface 60 compresses the sponge, releasing the air and air freshener stored within it through or between the ventilation unit or units 20 and 30 and/or the base unit 53, and out into the external environment 5.

When the pump handle 11 is released, the plate 60 lifts, the sponge 70 decompresses, and fragrance from the air freshener enclosure 40 is drawn into the sponge 70 from the resulting pump action. This embodiment may also combine the sponge 70 and air freshener enclosure 40 in the base unit 53, or release fragrance by drawing apart the upper and lower ventilation units 20 and 30 upon pump action 11b. Alternatively, fragrance may be released by drawing apart the upper ventilation unit 20 from the base unit 53 with or without the use of ventilation holes 21. Upon pump action 11b, hand lotion 52 is dispensed through the inner spout tube 12 and out the pump handle spout 11a.

Optionally, the hand lotion pump handle 11 may be rotated to turn off dispensing hand lotion 11a by use of an optional valve 15 (illustrated schematically in FIG. 2) at the joint of the pump handle 11 and the inner spout tube 12, as is known in the art. Thus, the pump action of the handle 11b can be used to indirectly power air freshener dispersion without dispensing hand lotion. Optionally and similarly, the hand lotion pump handle 11 may be rotated to prevent transfer of mechanical energy from pump action 11b to the mechanical energy transfer device to prevent active dispersion of air freshener while dispensing hand lotion.

Figure 3:
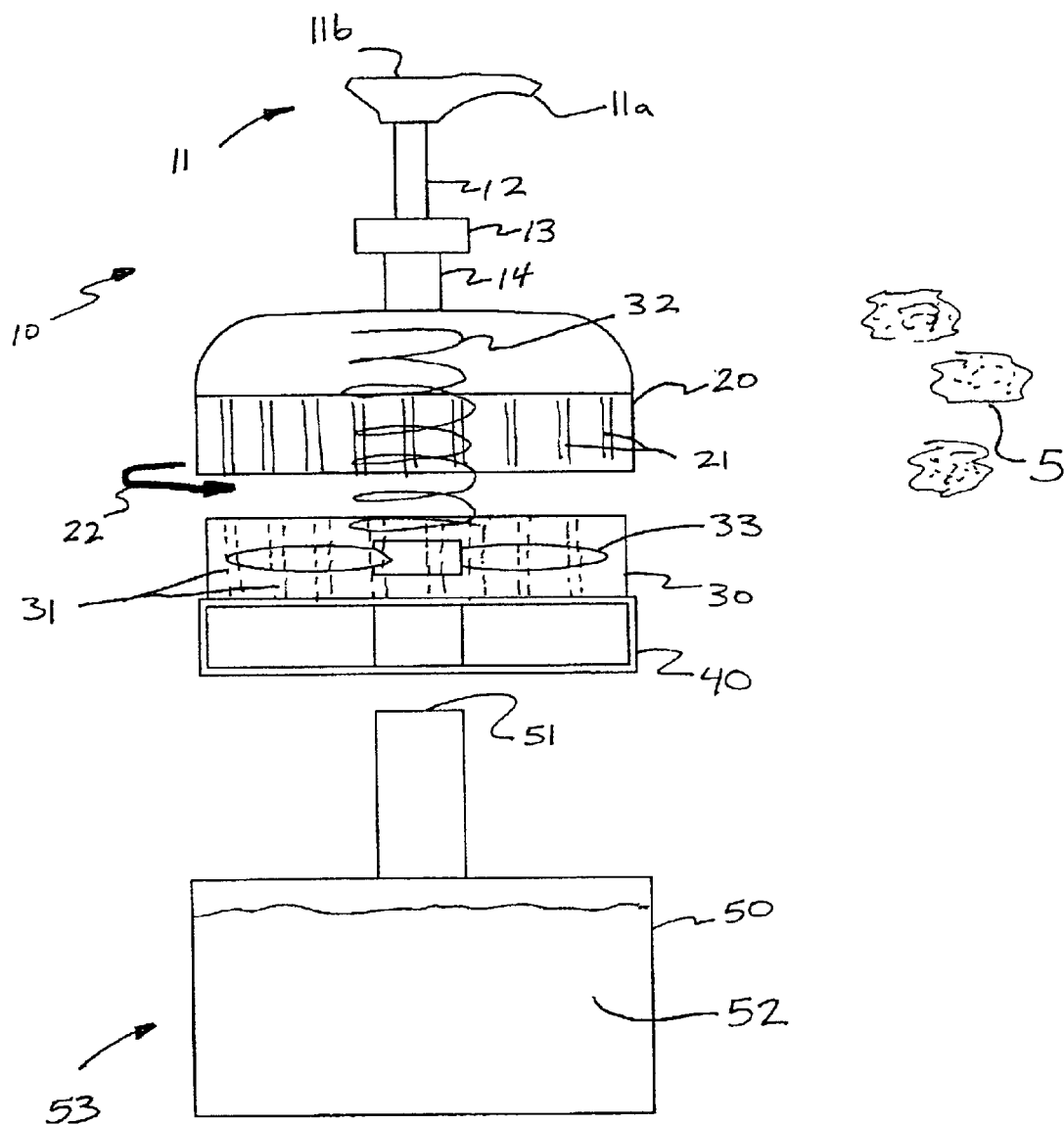
FIG. 3 is an exploded perspective view of a third embodiment of a hand lotion and air freshener dispenser with active dispersion of air freshener using a fan method.
Figure 4:
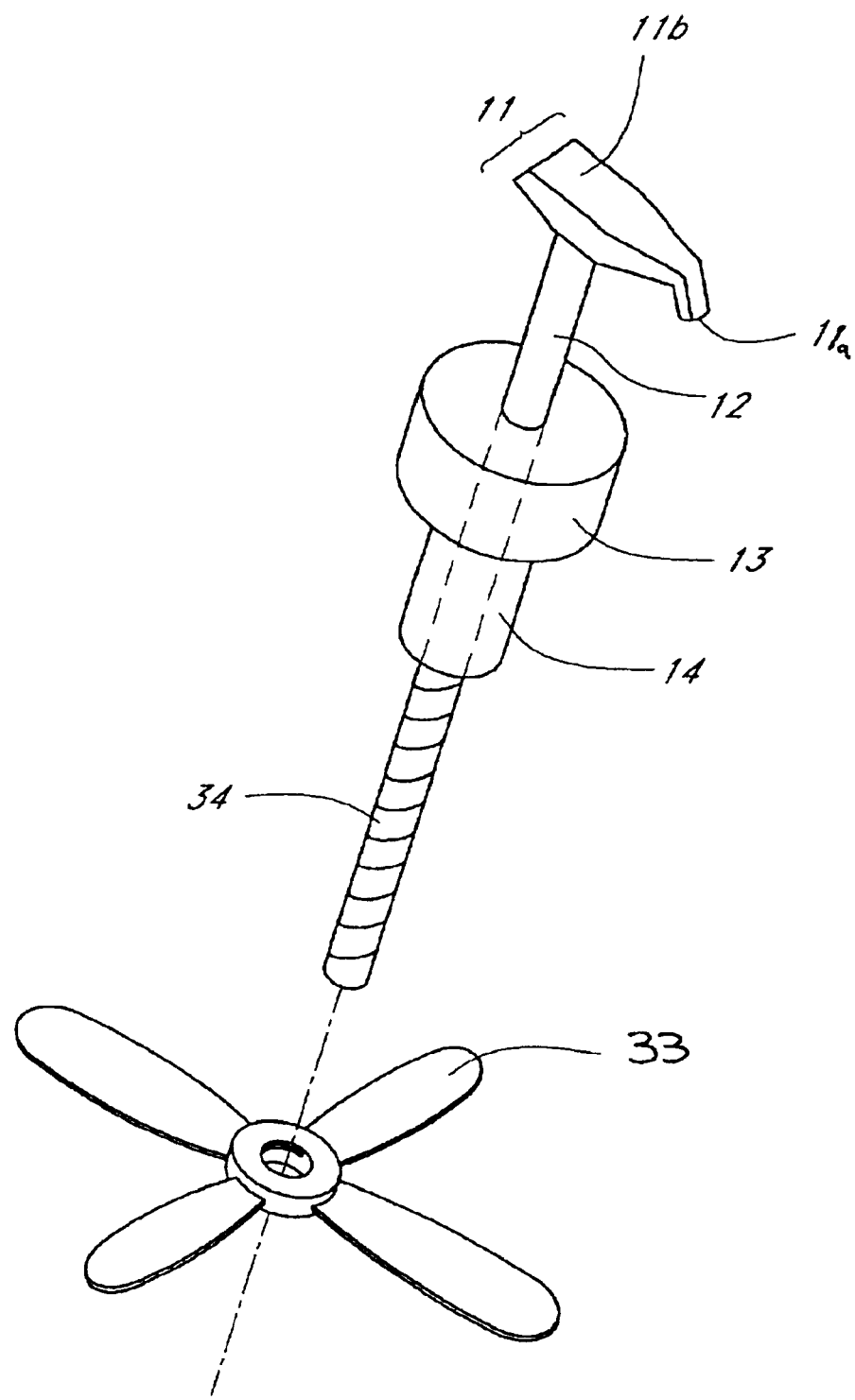
FIG. 4 is an exploded perspective view of the fan mechanism of the dispenser of FIG. 3.
Figure 5:
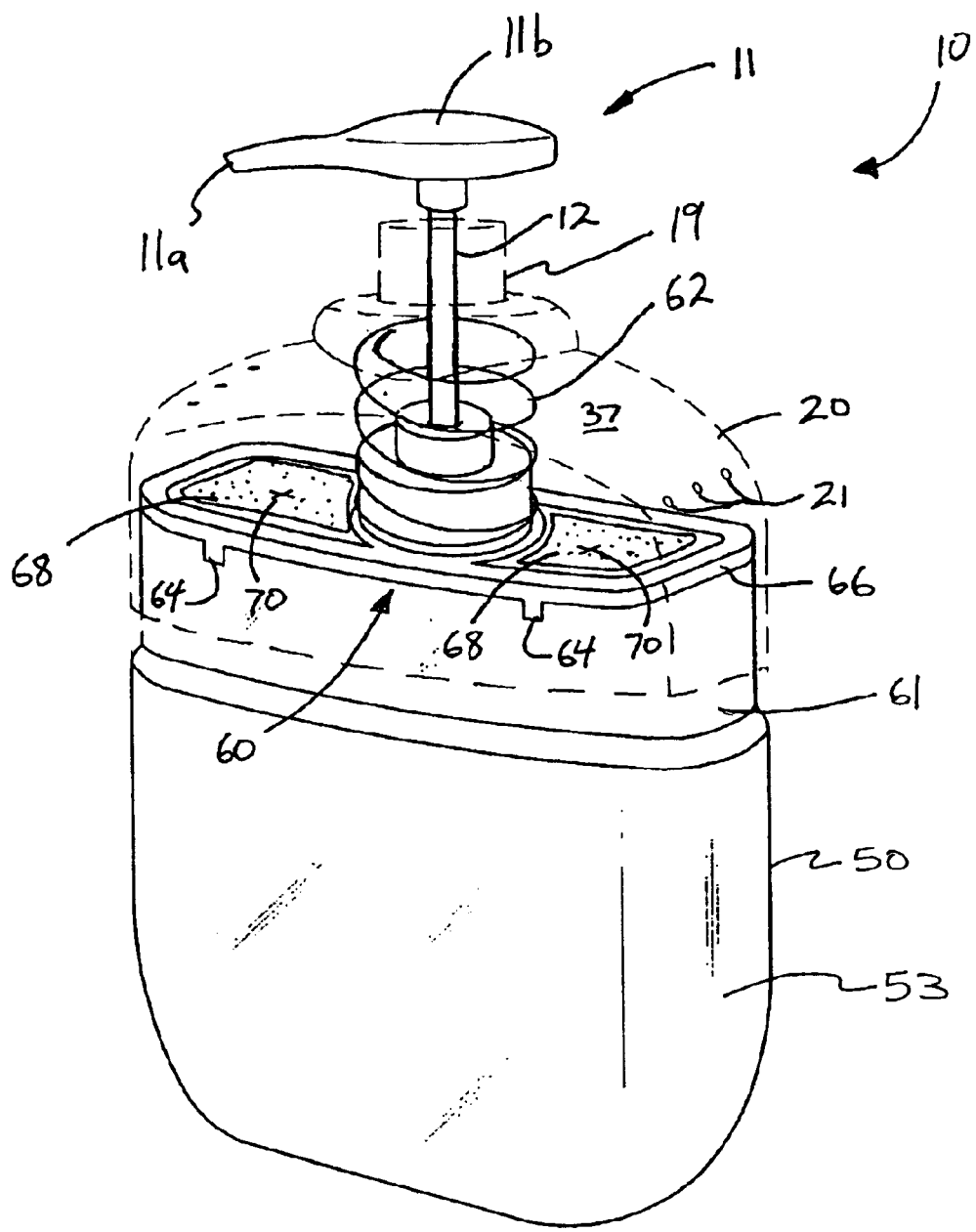
FIG. 5 is a perspective view of a fourth embodiment of a hand lotion and air freshener dispenser with active dispersion of air freshener using a manual pump method.

In FIGS. 3 and 4, another embodiment of a preferred dispenser 10 is shown. In this embodiment, the lower vent unit 30 may also contain a mechanical fan assembly 55, which comprises: a spring 32, a fan 33, and a helical gear 34 (FIG. 5). The helical gear 34 may be attached to, or defined by the inner spout tube 12 and mates with helical threading of the fan 33 to translate linear motion of the inner spout tube 12 into rotational motion of the fan 33. As the fan 33 turns 33a, an air freshener enclosure 40 evaporates more aggressively due to the action of the fan 33 and disperses through or between the optional lower 30 and/or upper 20 vent units, or between the upper vent unit 20 and base unit 53, into the surrounding environment 5.

Upon compression of the pump handle 11, in addition to turning the fan 33, the inner spout tube 12 and optional outer spout tube 14 are moved in a manner where the optional outer spout tube 14, or alternatively the inner spout tube 12, compresses the spring 32. Upon release of the pump handle 11, the spring 32 assists in restoring the dispenser 10 to its original position and prepares it for further use. By adjusting the helical gear 34, manually adjusting 22 the upper vent, or placing a stronger or weaker air freshener enclosure 40 in the invention, the rate of evaporation and strength of fragrance dispersed into the external environment 5 can be optionally adjusted.

FIG. 5 illustrates an additional embodiment of a preferred dispenser in which air freshener is actively dispensed upon user-initiated dispensing of hand lotion. In addition, the dispenser of FIG. 5 is capable of actively dispensing air freshener independently of dispensing hand lotion. This arrangement advantageously permits both simultaneous dispensing of air freshener and hand lotion for convenience, while allowing the same dispenser to be used for active dispensing of air freshener alone, at such times when odor control is desired while the use of hand lotion is not necessary or desired.

In the embodiment of FIG. 5, the upper vent, or hood, 20 partially covers the base unit 53 so as to create a cavity, or enclosure, 37 between them for placement of an air freshener assembly 60. The hood 20 includes an upwardly extending neck portion 19, which is contacted by the pump assembly 11 to move the hood 20 downward upon actuation of the pump assembly 11. Desirably, the base unit 53 includes a recessed upper portion 61 generally corresponding with the coverage of the hood 20. This allows the outer surface of the hood 20 to be substantially flush with the outer surface of the base unit 53 and provides for an aesthetically pleasing outward appearance.

Preferably, the hood 20 is engaged with the air freshener assembly 60 to substantially seal the cavity 37, while still allowing relative motion between the hood 20 and air freshener assembly 60. A spring 62 biases the hood 20 into an uppermost, or non-dispensing position. The illustrated spring 62 is a helical coil spring, however, other suitable types of springs may also be used. Preferably, the spring rate of the spring 62 is selected such that the hood 20 is quickly returned to the uppermost position when the pump handle 11 is released, yet allows the hood 20 to be moved into the dispensing position without requiring excessive downward pressure.

The air freshener assembly 60 is supported on the upper surface of the base unit 53. The hand lotion enclosure opening 51 extends upward through a central opening 64 in the air freshener assembly 60. Preferably, the hand lotion enclosure opening 51 is defined by a substantially cylindrical neck 54 and communicates with the interior space of the base unit 53. The neck 54 preferably includes external threads 56 that mate with internal threads 75 of a threaded cap 76 of the pump 11.

Preferably, the air freshener assembly 60 includes a plurality of tabs 64 extending downward over an upper portion of the base unit 53. The inner surfaces of each tab 64 defines an abutment surface which contacts the base unit 53 and inhibits the air freshener assembly 60 from rotating relative to the base unit 53. Preferably, four tabs 64 are provided with two on each side spaced from the central axis of the dispenser. Advantageously, this feature allows a threaded pump assembly to be assembled to the base unit 53 without causing rotation of the air freshener assembly 60.

Figure 6:
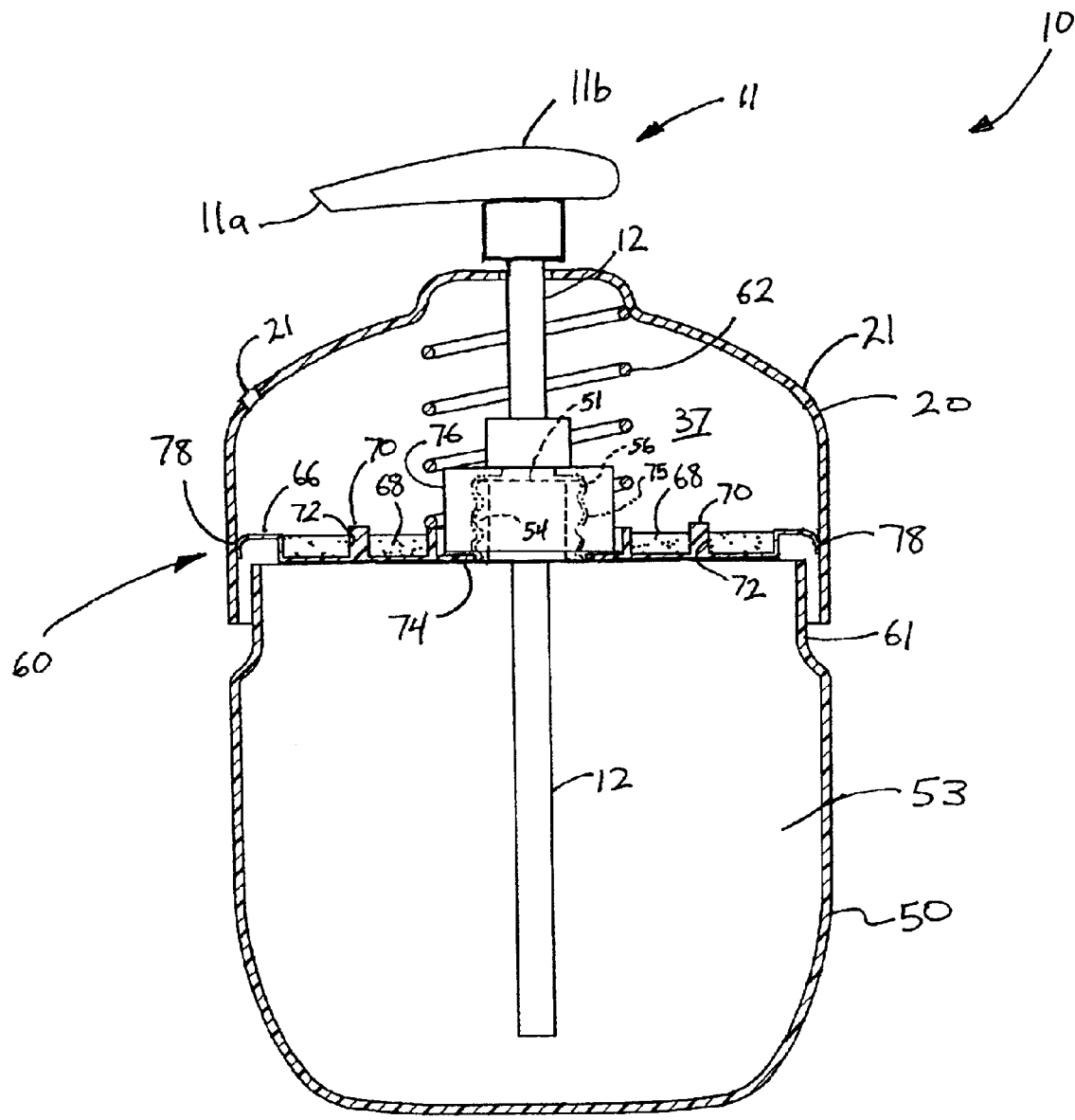
FIG. 6 is a partial cross-section of the dispenser of FIG. 5.

FIGS. 6–9, an alternative embodiment of a dispenser 10 is shown in partial cross-section. The dispenser 10 of FIG. 6 is similar to the dispenser of FIG. 5, with the exception that the neck portion 19 of the hood 20 has been omitted. However, the dispenser 10 of FIGS. 6–9 may optionally include a neck portion 19, if desired, while still performing substantially as described. The air freshener assembly 60 comprises a tray 66 which supports two carrier pads 68. The carrier pads 68 are preferably made of a polyester matrix and carry the supply of air freshener. However, other suitable, preferably porous, carrier materials may be used. A pair of projections, or support posts, 70 extend upward from the upper surface of the tray 66. The support posts 70 pass through an aperture 72 in the carrier pads 68 to position the pads 68 with respect to the tray 66 and prevent the pads 68 from moving during shipment or use of the dispenser 10. However, the support posts 70 permit the carrier pads 68 to be deliberately removed so that the pads 68 may be replaced. Preferably, the support posts 70 have a generally "X" shaped cross-section (FIG. 5) for ease of manufacturing, however, other suitable configurations may also be utilized.

A central flange portion 74 of the tray 66 is held between the upper surface of the base assembly 53 and a threaded cap 76 of the pump 11 thereby securing the tray 66 to the base assembly 53. The tray 66 defines a lip 78 about its periphery. The lip 78 is slideably engaged with the inner surface of the upper vent unit 20 to substantially seal the cavity 37, as described above. Preferably, the lip 78 is curved to allow easier movement of the hood, or upper vent, 20.

Figure 7:
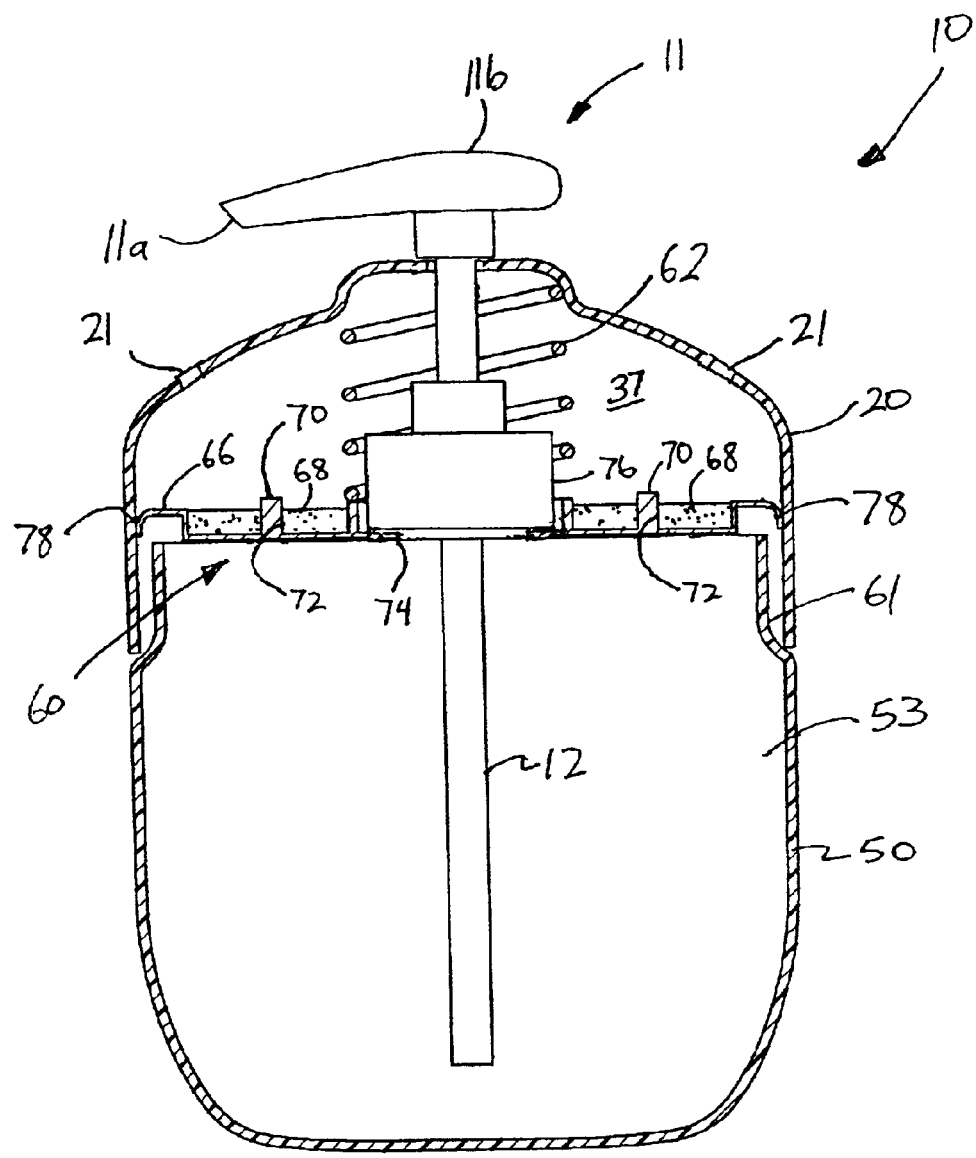
FIG. 7 is a partial cross-section of the dispenser of FIG. 5 in a dual dispensing position.

With reference to FIG. 7, the dispenser of FIG. 5 is illustrated in a dual dispensing mode. When the pump handle 11 is pressed downward to dispense hand lotion, the upper vent 20 is simultaneously moved downward. As a result, the volume of the cavity 37 is decreased, thereby expelling a portion of air within cavity 37, which contains fragrance, through the vents 21. Preferably, the downward travel of the upper vent unit 20 is approximately ¾ inches, however, other suitable travel distances may also be used. Thus, in the dual dispensing mode of FIG. 7, fragrance is actively dispensed simultaneously with the dispensing of hand lotion. Additionally, the fragrance is dispensed by the same downward pressure that dispenses the hand lotion.

Additionally, when the pump handle 11 and vent unit 20 are moved downward, the spring 62 is compressed. Upon release of the pump handle 11, the stored energy within the spring 62 is released thereby moving the vent unit 20 relative to the base unit 53 so as to increase the volume of the cavity 37. A fresh supply of air is drawn into the cavity 37 through the vents 21. The fresh air drawn into the cavity 37 increases the rate of evaporation of the air freshener supply within the carrier pads 68, thus increasing the fragrance within the cavity 37 and preparing the dispenser 10 for further use.

Figure 8:
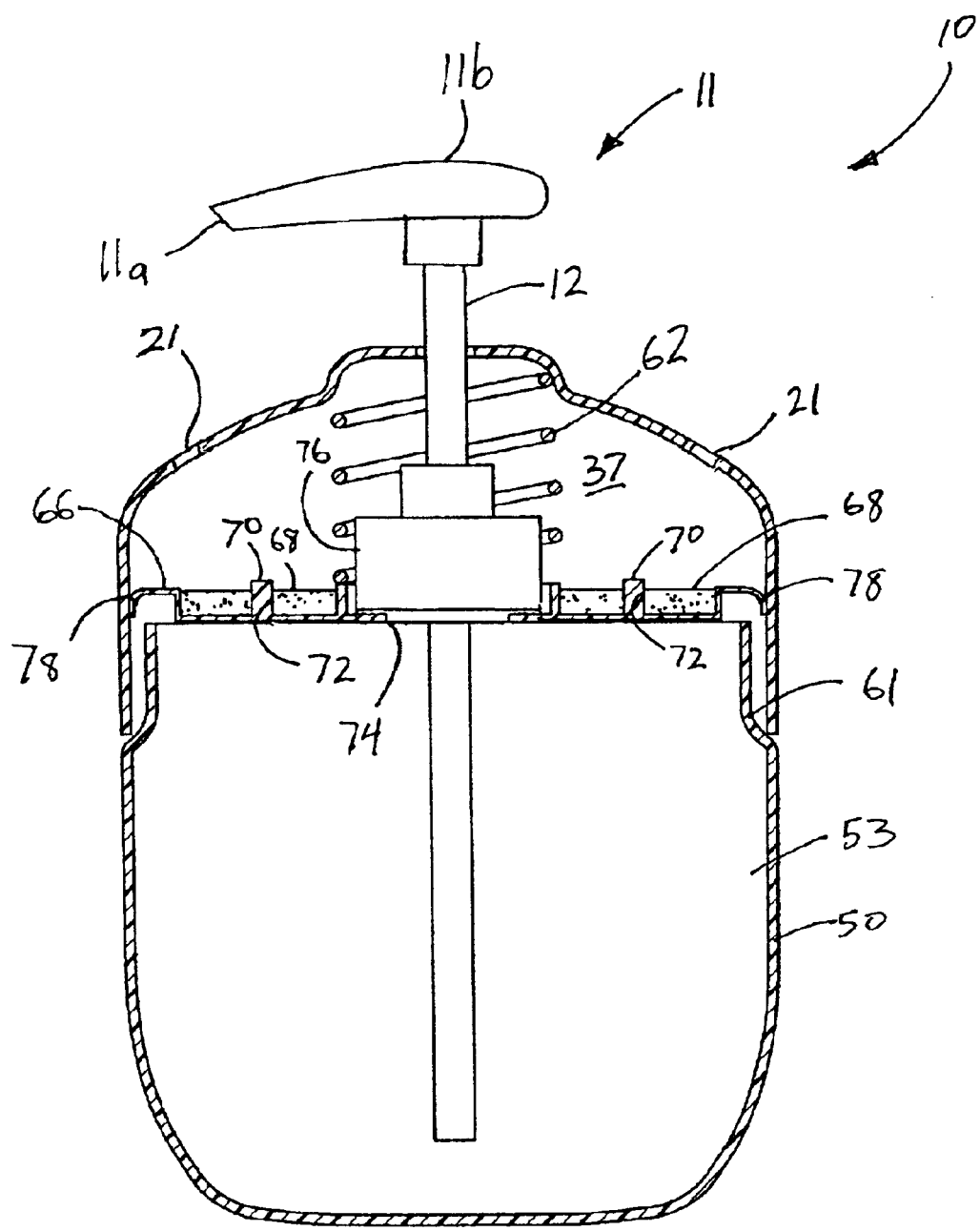
FIG. 8 is a partial cross-section of the dispenser of FIG. 5 in an air freshener only dispensing position.

With reference to FIG. 8, the dispenser of FIG. 5 is illustrated in an air freshener dispensing mode. In this mode, a downward pressure is applied to the upper vent unit 20 thereby moving the vent unit 20 in a downward direction while the pump handle 11 remains in an uppermost, or non-dispensing position. Air freshener is dispensed from the cavity 37 in a manner substantially as described above, without dispensing hand lotion.

Figure 9:
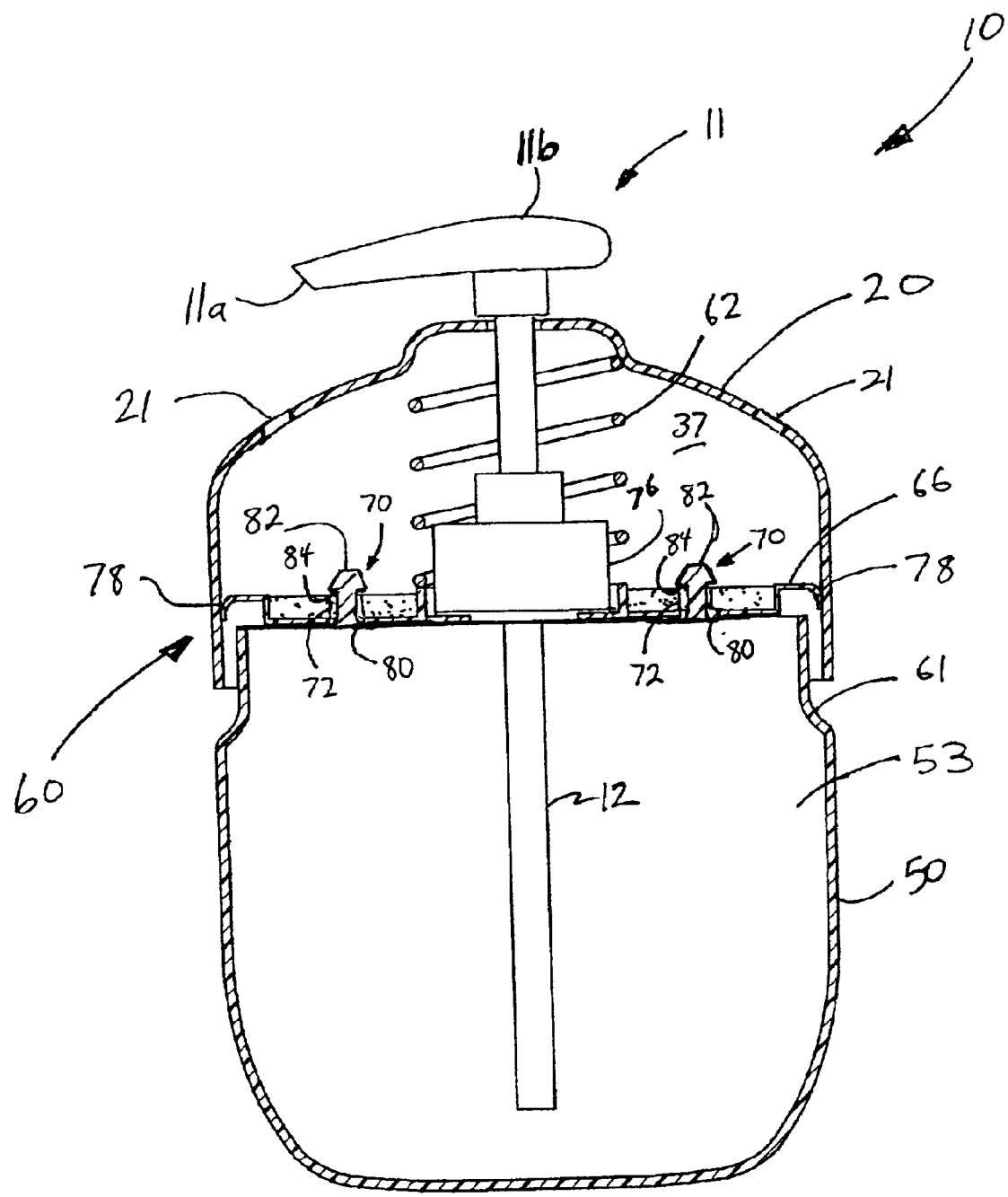
FIG. 9 is a partial cross-section of an alternative manual pump dispenser arrangement including support posts having retention heads for retaining carrier pads carrying air freshener.

FIG. 9 is a dispenser substantially identical to the dispenser of FIG. 5, except that the support posts 70 originate from the base unit 53, rather than being connected to the tray 66. The support posts 70 pass through corresponding apertures 80 in the tray 66. In addition, a retention head 82 is provided on the upper end of each support post 70. Each retention head 82 defines a retention surface 84 for retaining the carrier pad 68 onto the support post 70.

The retention heads 82 are preferably sized slightly larger than the apertures 72 of the carrier pads 68 such that the carrier pads 68 can be assembled onto the support posts 70 over the retention heads 82, while the retention surfaces 84 provide resistance against the carrier pads 68 being removed from the support posts 70. Advantageously, with such an arrangement, accidental removal of the carrier pads 68 by young children is inhibited.

Figure 10:
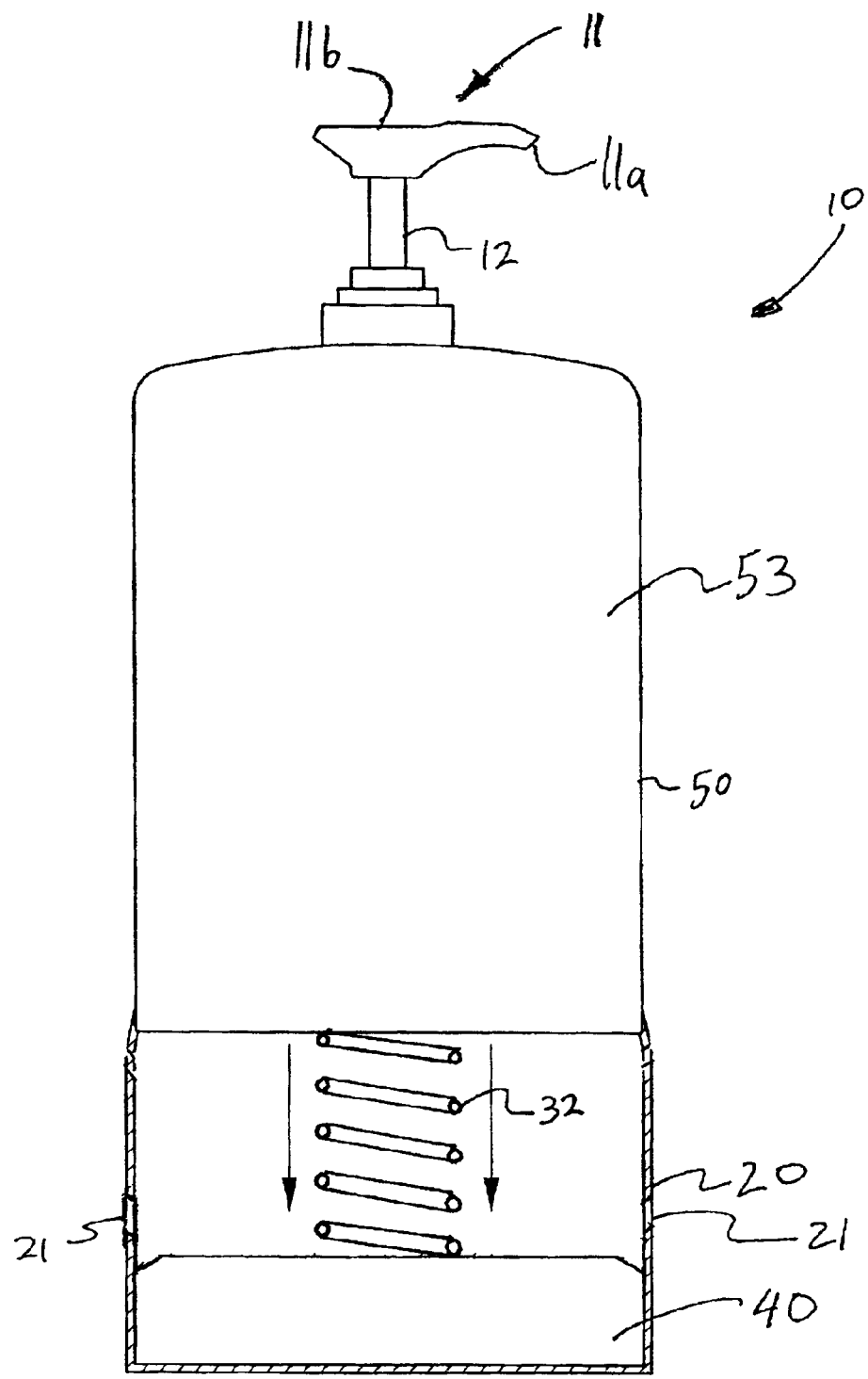
FIG. 10 is an additional embodiment of a dual dispenser, wherein hand lotion and soap are separately dispensable.

FIG. 10 is an additional embodiment of an active air freshener dispenser 10. In the illustrated embodiment, a vent unit 20 is constructed to slidingly receive the base unit 53 of the dispenser 10. Preferably, an air freshener enclosure 40, as described above, is placed within a cavity 37 defined between the vent unit 20 and the base unit 53. A spring 32 is operably positioned between the vent unit 20 and the base unit 53 to bias the base unit 53 into an upward position. The pump handle 11 may be depressed to dispense hand lotion in a known manner. The base unit 53 may be pressed downward to actively dispense air freshener in a manner substantially as described above. The spring 32 advantageously assist the base unit 53 in moving to an upward position, thus preparing the dispenser 10 for further use.

Advantageously, the vent unit 20 may be configured to receive a standard, commercially available hand lotion dispenser. Thus, the standard dispenser would serve as the base unit 53. Such an arrangement would allow convenient replacement of the base unit 53 with a variety of products that are commercially available in a standard pump dispenser, such as hand soap or hand sanitizer, for example.

Figure 11:
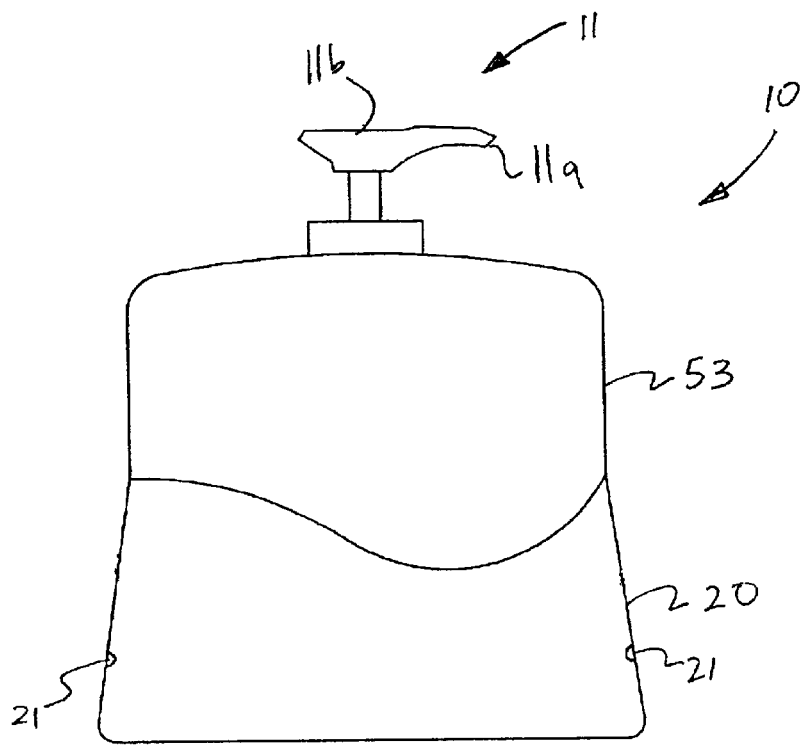
FIGS. 11 and 12 are front and side views, respectively, of an alternative dispenser similar to the dispenser of FIG. 10.
Figure 12:
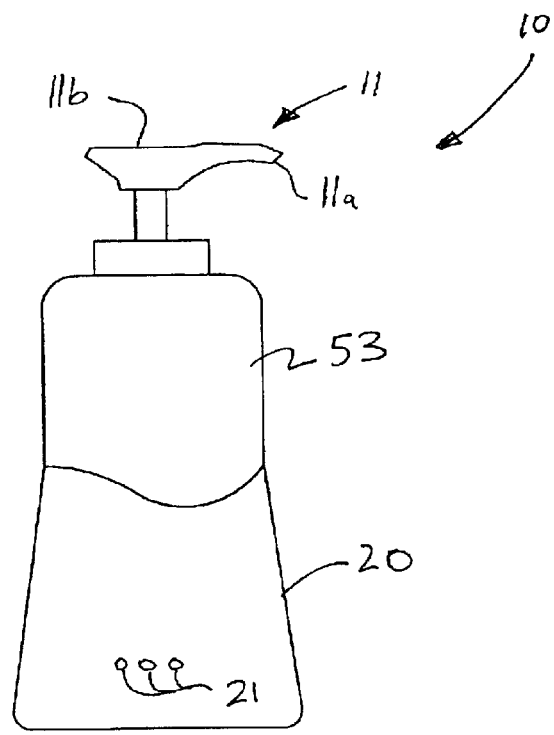

The vent unit 20 may be configured in a variety of shapes and sizes. For example, FIGS. 11 and 12 illustrate front and side views, respectively, of a vent unit 20 having a substantially trapezoidal shape in both the front and side views. In addition, the upper end of the vent unit 20 comprises a curvilinear shape for aesthetic appeal.

Figure 13:
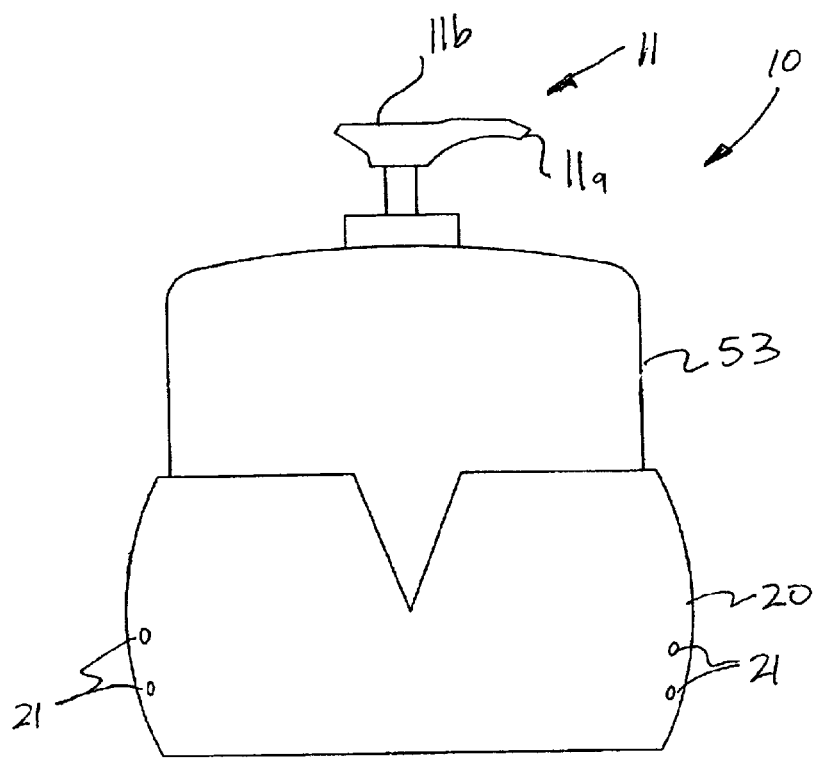
FIGS. 13 and 14 are front and side views, respectively, of another embodiment of a dispenser, which is similar to the dispenser of FIGS. 11 and 12.
Figure 14:
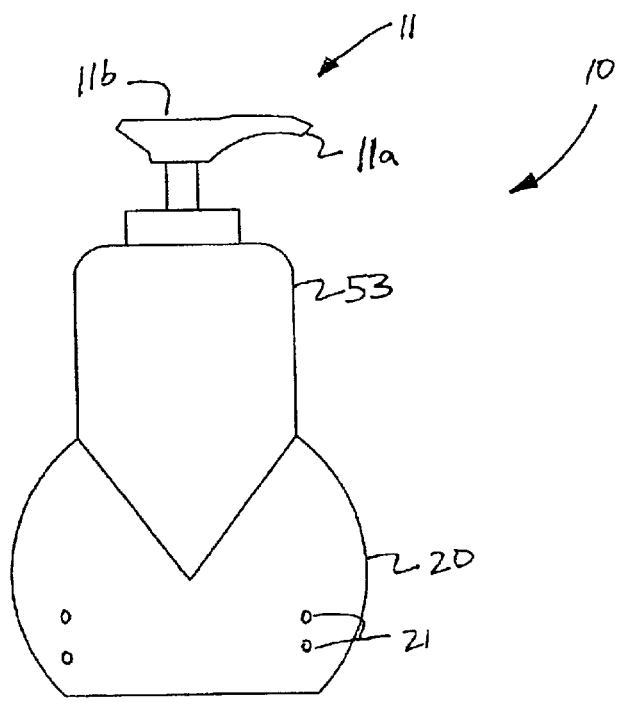

FIGS. 13 and 14 illustrate front and side views, respectively, of an alternative embodiment of a vent unit 20 for receiving a standard pump dispenser. The vent unit 20 of FIGS. 13 and 14 comprise a generally rounded shape in both the front and side views. In addition, the vent unit 20 includes a generally triangular central cutout in both the front and side of its upper end. Preferably, the triangular cutout is also provided in the back and hidden side.

Figure 15:
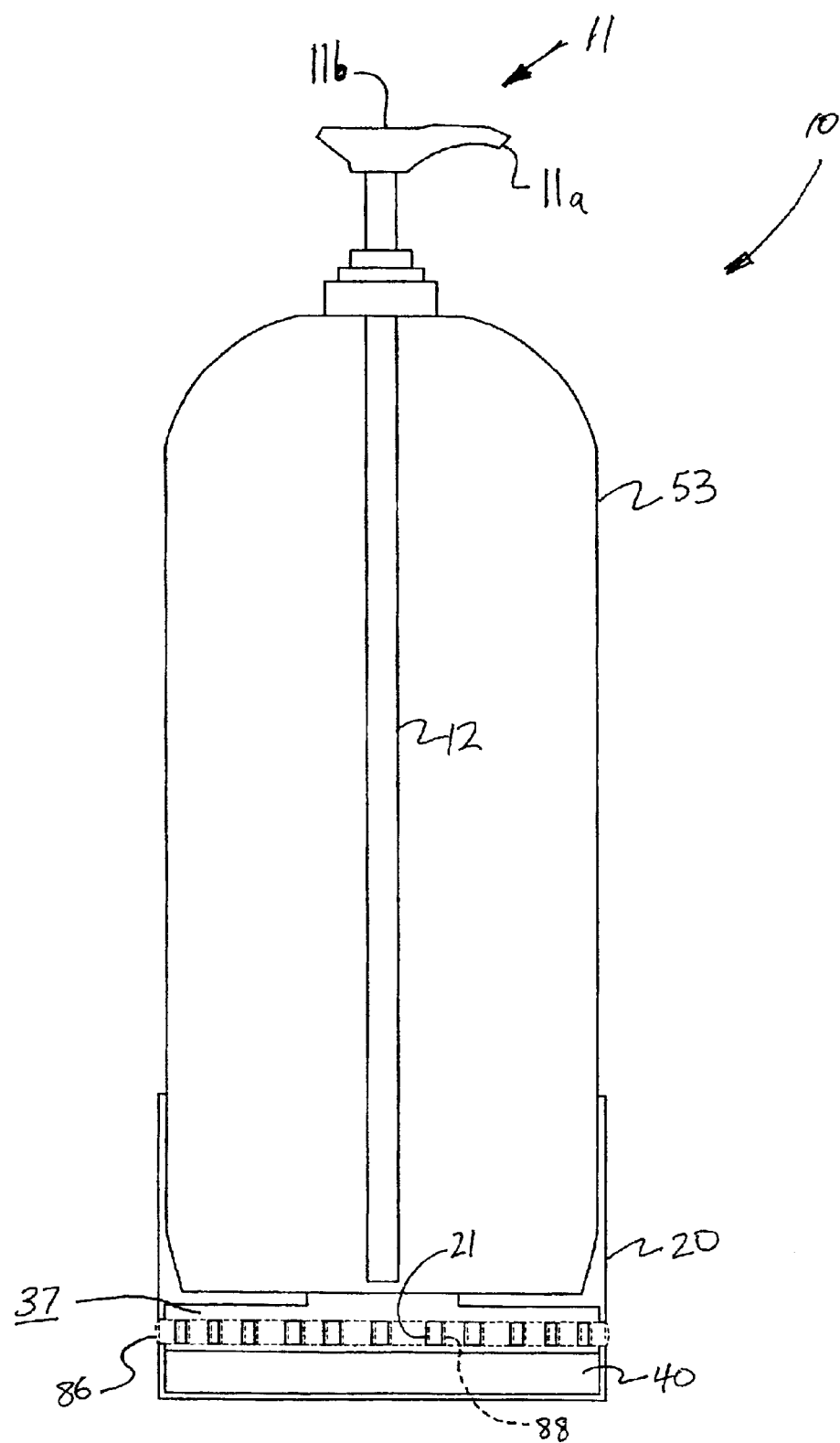
FIG. 15 is a dual dispenser in which hand lotion and soap are separately dispensable, with the air freshener being passively dispensed.

FIG. 15 illustrates a passive embodiment of a vent unit 20 for receiving a standard pump dispenser. The standard dispenser is received in the vent unit 20 in a fixed manner. That is, the cavity 37 defined therebetween is not variable in volume. However, an adjuster ring 86 is positioned over the vents 21 provided in the vent unit 20 to allow adjustment of the rate of air freshener dispensing. The adjuster ring 86 is rotatably engaged on the vent unit 20 and provided with a plurality of vents 88, which preferably correspond in size, shape and placement with the vents 21. The adjuster ring 86 can be moved from a fully closed position, in which the vents 21 are fully closed, to a fully open position, wherein the vents 21 and vents 88 are substantially aligned.

Preferred embodiments may take any shape practical for dispensing of hand lotion, soap or other personal care products. Thus, it is foreseen that the present invention could take the shape of any generally available consumer pump unit, a wall or table mounted unit, a portable unit for purse or automobile, or permanent unit with replaceable enclosures for air freshener and hand lotion. Such permanent units can be, for example, ceramic, glass, stone or plastic home design units with varying themes, pictures, or sculpted in any shape, or an ordinary commercial unit.

A preferred embodiment uses air freshener and hand lotion. Any commercially available hand lotion may be used. One preferred air freshener enclosure may contain a fragrance manufactured by Premier Specialties, Inc. of Middlesex, N.J. and may be fragrance #PSI-01842. If necessary, fragrance can be mixed with a volatile carrier such as an odorless hydrocarbon solvent (e.g., ISOPAR G manufactured by the Exxon Corp). As discussed above, however, in the United States limits are placed on Volatile Organic Compound (VOC) content in consumer products, including air fresheners. Therefore, an air freshener used in the United States must be designed and formulated to obey VOC limits.

Although this invention has been described in terms of certain preferred embodiments, other embodiments that are apparent to those of ordinary skill in the art are also within the scope of this invention. For example, the dispensing of other liquids, the electrification of the current invention, application to a vertical wall or horizontal countertop mountable unit, and use of other dispensing methods besides a pump are considered part of this invention. Accordingly, the scope of the invention is intended to be defined by the claims that follow.

I claim:

1. An assembly, comprising:
    a dispenser comprising a container and an actuator defining an actuation surface;
    a pourable compound within said container, wherein said compound is dispensible from said container upon manual manipulation of said actuation surface;
    a base defining a substantially flat mounting surface, an interior surface sized and shaped to receive and retain said dispenser, a location sized and shaped to receive a supply of air freshener;
    a supply of air freshener received by said location; and
    wherein said dispenser further comprises a pump and force exerted on said actuation surface moves said dispenser relative said base to accelerate the dispersal of air freshener from said supply of air freshener.

2. An assembly, comprising:
    a dispenser comprising a container and an actuator defining an actuation surface;
    a pourable compound within said container, wherein said compound is dispensible from said container upon manual manipulation of said actuation surface;

a base defining a substantially flat mounting surface, an interior surface sized and shaped to receive and retain said dispenser, a location sized and shaped to receive a supply of air freshener;

a supply of air freshener received by said location;

wherein said assembly can rest upon said mounting surface and wherein said base further defines at least one hole through which air freshener from said supply of air freshener can be dispersed.

3. An assembly, comprising:

a dispenser comprising a container and an actuator defining an actuation surface;

a pourable compound within said container, wherein said compound is dispensible from said container upon manual manipulation of said actuation surface;

a base defining a substantially flat mounting surface, an interior surface sized and shaped to receive and retain said dispenser, a location sized and shaped to receive a supply of air freshener;

a supply of air freshener received by said location; and wherein said container is positioned on top of said supply of air freshener.

* * * * *